(12) United States Patent
Venema

(10) Patent No.: US 8,222,389 B2
(45) Date of Patent: Jul. 17, 2012

(54) METHOD FOR LOWERING BOTH SEQUENCE VARIATIONS AND INCREASE OF BASE LINE EFFECTS IN A DIAGNOSTIC HYBRIDISATION ASSAY, ASSAY FOR PERFORMING SUCH A METHOD AND PROBE FOR USE IN THE ASSAY

(75) Inventor: Fokke Venema, Den Bosch (NL)

(73) Assignee: Biomerieux B.V., Boxtel (NL)

( * ) Notice: Subject to any disclaimer, the term of this patent is extended or adjusted under 35 U.S.C. 154(b) by 525 days.

(21) Appl. No.: 10/537,562

(22) PCT Filed: Dec. 2, 2003

(86) PCT No.: PCT/EP03/13676
§ 371 (c)(1), (2), (4) Date: Mar. 22, 2006

(87) PCT Pub. No.: WO2004/050911
PCT Pub. Date: Jun. 17, 2004

(65) Prior Publication Data
US 2006/0216708 A1    Sep. 28, 2006

(30) Foreign Application Priority Data
Dec. 3, 2002 (EP) .................................. 02080125

(51) Int. Cl.
*C07H 21/04* (2006.01)
*C12Q 1/68* (2006.01)
(52) U.S. Cl. ........................... 536/24.3; 435/6.11
(58) Field of Classification Search .............. None
See application file for complete search history.

(56) References Cited

U.S. PATENT DOCUMENTS

2003/0105320 A1* 6/2003 Becker et al. .............. 536/24.3
2003/0134307 A1* 7/2003 Beckman et al. ............ 435/6

FOREIGN PATENT DOCUMENTS

WO   WO 00/66604   11/2000
WO   WO 03/020952  3/2003

OTHER PUBLICATIONS

Majlessi, Mehrdad et al. Advantages of 2'-o-methyl oligoribonucleotide probes for detecting RNA targets. 1998. Nucleic Acids Research vol. 26, No. 9 pp. 2224-2229.*
Tsourkas, Andrew et al. Hybridization of 2'-O-methyl and 2'-deoxy molecular beacons to RNA and DNA targets. 2002 Nucleic Acids Research. vol. 30 No. 23 pp. 5168-5174.*
Goforth, Sarah. A Beacon in the Night. The Scientist May 2001 vol. 15 No. 11 p. 21.*
International Search Report for International patent application PCT/EP2003/13676 on Jun. 4, 2004.
Majlessi et al, "Advantages of 2'-0-methyl Oligoribonucleotide Probes for Detecting RNA Targets" *Nucleic Acids Research* 26(9): 2224-2229 (1998).
Tsourkas et al. "Hybridization Of 2'-0-Methyl and 2'-Deoxy Molecular Beacons To RNA and DNA Targets" *Nucleic Acid Research* 30(23): 5168-5174 (2002).
Huang and Li. "Characterization of the 5' to 3' Nuclease Activity of *Thermus aquaticus* DNA Polymerase on Fluorogenic Double-Stranded Probes" *Molecular and Cellular Probes* 23:188-194 (2009).
Kaiser et al. "A Comparison of Eubacterial and Archaeal Structure-Specific 5'-Exonucleases" *The Journal of Biological Chemistry* 274(30):21387-21394 (1994).
Lyamichev et al. "Structure-Specific Endonucleolytic Cleavage of Nucleic Acids by Eubacterial DNA Polymerases" *Science* 260:778-783 (1993).

* cited by examiner

*Primary Examiner* — Amanda Shaw
(74) *Attorney, Agent, or Firm* — Myers Bigel Sibley & Sajovec, PA

(57) ABSTRACT

The present invention relates to the use in a diagnostic hybridization assay of a molecular beacon probe for lowering: the effect of sequence variations in a nucleic acid analyte, and/or the IBL effect due to the possible opening of the stem-loop structure of a molecular beacon by way of (contaminants in the amplification) enzymes, which assay comprises the steps of contacting a set of primers and a sample containing the nucleic acid analyte to amplify the analyte and detecting the amplified analyte or its complement using a molecular beacon probe, wherein the molecular beacon probe comprises one or more nucleotides and/or nucleotide analogues that have an affinity increasing modification. The invention also relates to such molecular beacon probe and to a kit for performing a diagnostic assay using such molecular beacon probe.

24 Claims, 5 Drawing Sheets

Figure 5:
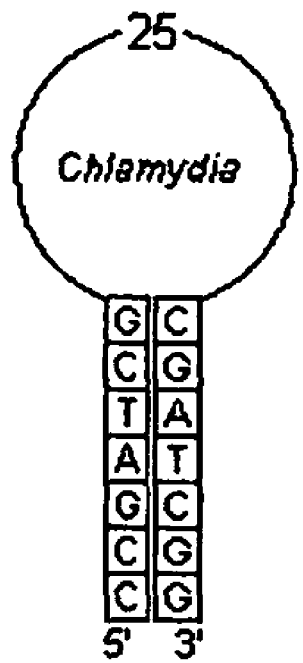

SEQUENCE LISTING

<160> NUMBER OF SEQ ID NOS: 12

<210> SEQ ID NO 1
<211> LENGTH: 26
<212> TYPE: DNA
<213> ORGANISM: Artificial
<220> FEATURE:
<223> OTHER INFORMATION: Molecular beacon Ref
<220> FEATURE:
<221> NAME/KEY: misc_feature
<222> LOCATION: (1)..(26)
<223> OTHER INFORMATION: n = inosine

<400> SEQUENCE: 1
atcaatgagg angctgcaga ntggga                                           26

<210> SEQ ID NO 2
<211> LENGTH: 26
<212> TYPE: DNA
<213> ORGANISM: Artificial
<220> FEATURE:
<223> OTHER INFORMATION: Molecular beacon Me-1
<220> FEATURE:
<221> NAME/KEY: misc_feature
<222> LOCATION: (1)..(26)
<223> OTHER INFORMATION: n = inosine;
<220> FEATURE:
<221> NAME/KEY: modified_base
<222> LOCATION: (4)..(5)
<223> OTHER INFORMATION: 2'-O-methyladenine
<220> FEATURE:
<221> NAME/KEY: modified_base
<222> LOCATION: (8)..(8)
<223> OTHER INFORMATION: 2'-O-methyladenine
<220> FEATURE:
<221> NAME/KEY: modified_base
<222> LOCATION: (11)..(11)
<223> OTHER INFORMATION: 2'-O-methyladenine
<220> FEATURE:
<221> NAME/KEY: modified_base
<222> LOCATION: (18)..(18)
<223> OTHER INFORMATION: 2'-O-methyladenine
<220> FEATURE:
<221> NAME/KEY: modified_base
<222> LOCATION: (20)..(20)
<223> OTHER INFORMATION: 2'-O-methyladenine

<400> SEQUENCE: 2
atcaatgagg angctgcaga ntggga                                           26

<210> SEQ ID NO 3
<211> LENGTH: 26
<212> TYPE: DNA
<213> ORGANISM: Artificial
<220> FEATURE:
<223> OTHER INFORMATION: Molecular beacon Me-2
<220> FEATURE:
<221> NAME/KEY: misc_feature
<222> LOCATION: (1)..(26)
<223> OTHER INFORMATION: n = inosine
<220> FEATURE:
<221> NAME/KEY: modified_base
<222> LOCATION: (4)..(5)
<223> OTHER INFORMATION: 2'-O-methyladenine
<220> FEATURE:
<221> NAME/KEY: modified_base
<222> LOCATION: (7)..(7)
<223> OTHER INFORMATION: 2'-O-methylguanine
<220> FEATURE:
<221> NAME/KEY: modified_base
<222> LOCATION: (9)..(10)
<223> OTHER INFORMATION: 2'-O-methylguanine
<220> FEATURE:

```
<221> NAME/KEY: modified_base
<222> LOCATION: (11)..(11)
<223> OTHER INFORMATION: 2'-O-methyladenine
<220> FEATURE:
<221> NAME/KEY: modified_base
<222> LOCATION: (13)..(13)
<223> OTHER INFORMATION: 2'-O-methylguanine
<220> FEATURE:
<221> NAME/KEY: modified_base
<222> LOCATION: (16)..(16)
<223> OTHER INFORMATION: 2'-O-methylguanine
<220> FEATURE:
<221> NAME/KEY: modified_base
<222> LOCATION: (19)..(19)
<223> OTHER INFORMATION: 2'-O-methylguanine
<220> FEATURE:
<221> NAME/KEY: modified_base
<222> LOCATION: (20)..(20)
<223> OTHER INFORMATION: 2'-O-methyladenine
<220> FEATURE:
<221> NAME/KEY: modified_base
<222> LOCATION: (23)..(24)
<223> OTHER INFORMATION: 2'-O-methylguanine

<400> SEQUENCE: 3
atcaatgagg angctgcaga ntggga                                    26

<210> SEQ ID NO 4
<211> LENGTH: 26
<212> TYPE: DNA
<213> ORGANISM: Artificial
<220> FEATURE:
<223> OTHER INFORMATION: Molecular beacon Me-7
<220> FEATURE:
<221> NAME/KEY: misc_feature
<222> LOCATION: (1)..(26)
<223> OTHER INFORMATION: n = inosine
<220> FEATURE:
<221> NAME/KEY: modified_base
<222> LOCATION: (5)..(5)
<223> OTHER INFORMATION: 2'-O-methyladenine
<220> FEATURE:
<221> NAME/KEY: modified_base
<222> LOCATION: (7)..(7)
<223> OTHER INFORMATION: 2'-O-methyllguanine
<220> FEATURE:
<221> NAME/KEY: modified_base
<222> LOCATION: (9)..(10)
<223> OTHER INFORMATION: 2'-O-methyllguanine
<220> FEATURE:
<221> NAME/KEY: modified_base
<222> LOCATION: (11)..(11)
<223> OTHER INFORMATION: 2'-O-methyladenine
<220> FEATURE:
<221> NAME/KEY: modified_base
<222> LOCATION: (13)..(13)
<223> OTHER INFORMATION: 2'-O-methyllguanine
<220> FEATURE:
<221> NAME/KEY: modified_base
<222> LOCATION: (16)..(16)
<223> OTHER INFORMATION: 2'-O-methyllguanine
<220> FEATURE:
<221> NAME/KEY: modified_base
<222> LOCATION: (18)..(18)
<223> OTHER INFORMATION: 2'-O-methyladenine
<220> FEATURE:
<221> NAME/KEY: modified_base
<222> LOCATION: (19)..(19)
<223> OTHER INFORMATION: 2'-O-methyllguanine
<220> FEATURE:
<221> NAME/KEY: modified_base
<222> LOCATION: (20)..(20)
<223> OTHER INFORMATION: 2'-O-methyladenine
<220> FEATURE:
<221> NAME/KEY: modified_base
<222> LOCATION: (23)..(25)
<223> OTHER INFORMATION: 2'-O-methyllguanine
```

-continued

```
<400> SEQUENCE: 4
atcaatgagg angctgcaga ntggga                                              26

<210> SEQ ID NO 5
<211> LENGTH: 26
<212> TYPE: DNA
<213> ORGANISM: Artificial
<220> FEATURE:
<223> OTHER INFORMATION: Molecular beacon Ref2

<400> SEQUENCE: 5
atcaatgagg aagctgcaga atggga                                              26

<210> SEQ ID NO 6
<211> LENGTH: 26
<212> TYPE: DNA
<213> ORGANISM: Artificial
<220> FEATURE:
<223> OTHER INFORMATION: Molecular beacon LNA1
<220> FEATURE:
<221> NAME/KEY: modified_base
<222> LOCATION: (1)..(1)
<223> OTHER INFORMATION: LNA nucleotide of adenine
<220> FEATURE:
<221> NAME/KEY: modified_base
<222> LOCATION: (15)..(15)
<223> OTHER INFORMATION: LNA nucleotide of thymine

<400> SEQUENCE: 6
atcaatgagg aagctgcaga atggga                                              26

<210> SEQ ID NO 7
<211> LENGTH: 26
<212> TYPE: DNA
<213> ORGANISM: Artificial
<220> FEATURE:
<223> OTHER INFORMATION: Molecular beacon LNA2
<220> FEATURE:
<221> NAME/KEY: modified_base
<222> LOCATION: (1)..(1)
<223> OTHER INFORMATION: LNA nucleotide of adenine
<220> FEATURE:
<221> NAME/KEY: modified_base
<222> LOCATION: (11)..(11)
<223> OTHER INFORMATION: LNA nucleotide of adenine
<220> FEATURE:
<221> NAME/KEY: modified_base
<222> LOCATION: (15)..(15)
<223> OTHER INFORMATION: LNA nucleotide of thymine

<400> SEQUENCE: 7
atcaatgagg aagctgcaga atggga                                              26

<210> SEQ ID NO 8
<211> LENGTH: 26
<212> TYPE: DNA
<213> ORGANISM: Human immunodeficiency virus type 1

<400> SEQUENCE: 8
atcaatgagg aagctgcaga atggga                                              26

<210> SEQ ID NO 9
<211> LENGTH: 26
<212> TYPE: DNA
<213> ORGANISM: Human immunodeficiency virus type 1

<400> SEQUENCE: 9
attaatgaag aagctgcaga gtggga                                              26
```

```
<210> SEQ ID NO 10
<211> LENGTH: 26
<212> TYPE: DNA
<213> ORGANISM: Human immunodeficiency virus type 1

<400> SEQUENCE: 10
atcaatgagg aagcagcaga ctggga                                          26

<210> SEQ ID NO 11
<211> LENGTH: 26
<212> TYPE: DNA
<213> ORGANISM: Human immunodeficiency virus type 1

<400> SEQUENCE: 11
atcaatgatg aagcagcaga ttggga                                          26

<210> SEQ ID NO 12
<211> LENGTH: 26
<212> TYPE: DNA
<213> ORGANISM: Human immunodeficiency virus type 1

<400> SEQUENCE: 12
atcaatgagg aagcggcaga ttggga                                          26
```

METHOD FOR LOWERING BOTH SEQUENCE VARIATIONS AND INCREASE OF BASE LINE EFFECTS IN A DIAGNOSTIC HYBRIDISATION ASSAY, ASSAY FOR PERFORMING SUCH A METHOD AND PROBE FOR USE IN THE ASSAY

RELATED APPLICATION INFORMATION

This application claims the benefit under 35 U.S.C. §371 of PCT Application Serial No. PCT/EP2003/013676, filed Dec. 2, 2003, the disclosure of which is incorporated by reference herein in its entirety, which claims the benefit of European Application Serial No. EP 02080125.4, filed Dec. 3, 2002, the disclosure of which is incorporated by reference herein in its entirety.

The present invention relates to a method for lowering the effect of sequences variations in diagnostic hybridisation assays that use a nucleic acid probe to detect an amplified nucleic acid analyte. The present invention also relates to a method for lowering the unwanted IBL (Increase of Base Line) effect, which limits the use of molecular beacons in diagnostic hybridisation assays. The invention further relates to the assays thus obtained and to probes for use in such assays, the diagnostic assays and probes using at least one of these two methods for lowering undesirable consequences on diagnostic results. Many diagnostic assays are based on the amplification of a nucleic acid molecule or part thereof with the help of primers and the detection of the amplified material by means of a probe. Under the appropriate reaction conditions, the primers hybridise to the analyte to be detected and initiate amplification of the target sequence. This will lead to the generation of amplicons.

Meanwhile various amplification techniques have been developed, such as PCR, LCR, NASBA, TMA, RCR, 3SR and SDA, and are now well known to the person skilled in the art. Relevant information on these techniques can be found in various documents:

PCR (Polymerase Chain Reaction), described in U.S. Pat. No. 4,683,195, U.S. Pat. No. 4,683,202 et U.S. Pat. No. 4,800,159, and its derivate RT-PCR (Reverse Transcription PCR), to perform RNA amplification disclosed particularly in EP-B-0.569.272, LCR (Ligase Chain Reaction), exposed in EP-A-0.201.184, NASBA (Nucleic Acid Sequence-Based Amplification) described in WO-A-91/02818, et TMA (Transcription Mediated Amplification) disclosed in U.S. Pat. No. 5,399,491.

RCR (Repair Chain Reaction) exposed in application WO-A-90/01069,

3SR (Self Sustained Sequence Replication) well explained in application WO-A-90/06995.

During or after amplification of the analyte or part thereof, the presence or amount of amplicons generated should be detected. This can be done with various known techniques such as separation of the sample on a gel with subsequent blotting and probing. This can only be done after the amplification is finished.

In a homogeneous procedure, amplification and detection occur without separating the reaction components. Amplicons are detected in the course of the amplification. Thus, the generation of amplicons can be monitored real-time and the data thus obtained can be used to determine the presence or absence or the amount of the amplicon. One type of probe that is very useful in such homogeneous techniques is the molecular beacon.

Molecular beacons are single-stranded oligonucleotides having a stem-loop structure. The loop portion contains the sequence complementary to the target nucleic acid (either DNA or RNA). The stem is formed due to hybridisation of the complementary sequence of the 3' end with the 5' end. The stem can be unrelated to the target and is double-stranded. One arm of the stem is labelled with a fluorescent dye (fluorophore), whereas the other one is coupled to a quenching molecule. In the stem-loop state the probe does not produce fluorescence because the energy of the fluorophore is transferred to the quenching molecule. When the molecular beacon hybridises to the target the stem-loop structure is lost and the quencher and fluorophore are separated. At that stage the fluorescence emitted by the fluorophore can be detected and quantified. It was recently observed by the applicant during the development of assays using MB's for the detection of target, that the quality of commercially available enzymes (e.g. T7 RNA polymerase (T7)) that are normally used during the amplification process differs. This led to the observation that different batches of T7, even from the same supplier, with the same specific activity and volume activity, had different levels of unwanted opening of MB's (IBL effect) if these MB's consist of natural deoxyribonucleotides. Thus a fluorescent signal appears even in the absence of specific targeted sequences in the biological sample to be tested, generating possible false positive result.

If skilled people could have linked the IBL effect to T7 itself, our investigations showed unexpectedly that it is not the T7 itself that generates this phenomenon, but that it is more likely at least an unknown contaminant in the T7, which can differ from batch to batch. In line with the publications exposed in relation with the method for lowering the effect of sequences variations in diagnostic hybridisation assays, the man skilled in the art could have concluded to the usefulness of a MB that consists of only 2'-O-methyl derivatives to overcome the IBL effect. The applicant observed unexpectedly, that it is much more efficient to introduce less 2'-O-methyl groups in the MB, and that substituting all natural deoxyribonucleotides leads to non or less functional MB's.

Concerning the effect of sequences variations in diagnostic hybridisation assays, the amplicons generated in the amplification reaction can be detected quantitatively or qualitatively. In the former case the amount of amplicons generated is quantified. In a qualitative assay only the presence or absence of the analyte is determined.

Sequence variations (polymorphisms) in the analyte can lead to under-quantification thereof. Also in case of qualitative assays sequence variations can result in false negatives. It is generally assumed that this is caused by mismatches between the analyte and the primers used to amplify the analyte or by the structure of the analyte, which causes primers not to bind.

It is known that various polymorphic pathogenic strains of viruses exist as for example for the analytes HIV, CMV, HSV etc. These polymorphic strains differ from each other usually by one or more nucleotides. When a primer differs from the analyte it does not fit very well which leads to a reduced amplification. When the analyte is not linear but has a particular structure, it is less accessible by the primer, which in turn also leads to a reduced amplification.

In addition, sequence differences between the amplified target sequence of the analyte and the probe used for detection further lower the efficiency of detection. Analytes with polymorphisms, are thus less well detected than analytes that match perfectly with the consensus sequence of the probe. However, detection is usually performed at lower temperatures than the amplification, and therefore the negative effect of mismatches between probe and target is expected to be far less than is caused by differences between primer and analyte.

The probe can be optimised to fit known polymorphisms. However, in the case of unknown polymorphisms this is not possible. This is particularly a problem since new, unknown polymorphisms are continuously generated, which hamper a reliable detection or quantification especially in the case of HIV.

In the research that led to the invention it was now found that in a NASBA amplification reaction of a (clinical) sample of an HIV virus with an unknown polymorphism no signal or lower signals were generated in the Molecular Beacon detection system. However, surprisingly amplicons could be detected when the Molecular Beacon probe was modified such that the melting temperature of the probe with the analyte was increased. This led to the unexpected conclusion that amplicons were indeed produced but not or only partially detected.

Concerning the IBL effect, the applicant also observed that this effect, due to the unwanted opening of the stem of the molecular beacons by the action of contaminant(s) present within the enzymes' batch, such as the ones used during NASBA amplification (AMV-RT, T7 RNA polymerase and RNase H), can be lowered when the stem of the Molecular Beacon probes was modified in such a way that the nucleotides in the stem was partly replaced by 2'-O-Methyl derivatives.

Modification of the nucleotides constituting the probes and especially the Molecular Beacon probes is a widespread technique as can be derived from the publications mentioned below.

For example in application WO-A-00/66604, the use of L-ribo-LNA nucleotides in constructing oligonucleotides is exposed. L-ribo-LNAs can be used as a mean to increase affinity and/or specificity of the probes and also to equalize the affinity of different oligonucleotides for their complementary sequences. A special form of this LNA in combination with short probes could also be used to discriminate between RNA and DNA probes. This can be accomplished by replacing selected nucleosides in the oligonucleotide with L-ribo-LNAs to improve diagnostic and molecular biology procedures.

The publication of Majlessi et al. (vol. 26, no. 9, 1998, pages 2224-2229 (XP002241700)) describes linear probes containing only 2'-O-Methyl oligonucleotides The goal of this publication is limited to a comparison between 2'-O-Methyl probes and normal 2'-deoxy probes, to show the improved Tm and the faster hybridization kinetics of the modified probes. They come to the conclusion that the variation of Tm values between matched and mismatched duplexes were much greater for 2'-O-Methyl probes than 2'-deoxy probes. This statement is true for all probes length examined (8-26 nucleotides) and the difference in Tm was most dramatic when probe lengths were 16 bases or less.

Another publication of Tsourkas et al. (vol. 30, no. 23, 1 Dec. 2002, pages 5168-5174 (XP002241701)) proposes to decrease the nuclease degradation of Molecular Beacons. For this purpose, they protect the MB's and enhance the affinity between probes and RNA at the same time by replacing all 21-deoxy nucleotides of a Molecular Beacon probe by 2'-O-Methyl oligonucleotides.

In a document of Brown-Driver et al. (vol. 9, no. 2, April 1999 (1999-04), pages 145-154 (XP09008881)), it is proposed to use modified antisense oligonucleotides complementary to HCV RNA in place of unmodified oligonucleotides, to inhibit HCV translation. One of the modified oligonucleotide, which is a good candidate among others, is the 2'-O-Methyl oligonucleotide. As set for the two abovementioned publications, all the nucleotides of each modified antisense oligonucleotide are constituted by 2'-O-Methyl nucleotides. The consequence of this structure is the increase of the affinity and then the strong binding between the target and the modified oligonucleotides.

In contrast to the here above mentioned prior art, the invention shows that Molecular Beacon probes incorporating just a few 2'-O-Methyl nucleotides per probe (between 6 and 15 of the hybridising 26 nucleotides) i.e. between 23% and 58% of incorporation) are useful for RNA targets detection and even more efficient than oligonucleotides which are totally substituted with 2'-O-Methyl nucleotides.

Concerning the effect of sequences variations in diagnostic hybridisation assays, LNA analogues are also good candidates to reach the final result of this invention: Molecular Beacons, which are partially modified with LNA's, become a very versatile tool for lowering the dependency towards sequence variation of the target in diagnostic assays.

In the same way, the IBL effect due to the possible opening of the stem-loop structure of the Molecular Beacons by contaminant(s) present in the amplification enzymes mixture is lowered when these Molecular Beacon probes are partially modified with 2'-O-Methyl nucleotides. This led to the unexpected conclusion that with this improved structure the Molecular Beacon probes had a better stability and did not open spontaneously in the presence of (contaminants of the amplification) enzymes.

It is therefore the object of the present invention to lower the effects of sequence polymorphisms in an hybridisation assay by manipulation of the affinity between the probe and the analyte. This is achieved according to the invention by introduction into the probe of one or more nucleotides and/or nucleotide analogues that result in an increase of the affinity between the analyte and the probe.

The invention thus relates to the use in a diagnostic hybridisation assay of a probe, which could be a Molecular Beacon, for lowering the effect of sequence variations in a nucleic acid analyte, which assay comprises the steps of contacting a set of primers and a sample containing the nucleic acid analyte to amplify the analyte and detecting the amplified analyte or its complement by means of the probe, wherein the probe comprises one or more nucleotides and/or nucleotide analogues that have an affinity increasing modification and the diagnostic assay is for assessing the amount of analyte present in the sample.

The invention also relates to the use in a diagnostic hybridisation assay of a probe, which could be a Molecular Beacon, for lowering the effect of sequence variations in a nucleic acid analyte, which assay comprises the steps of contacting a set of primers and a sample containing the nucleic acid analyte to amplify the analyte and detecting the amplified analyte or its complement by means of the probe, wherein the probe comprises one or more nucleotides and/or nucleotide analogues that have an affinity increasing modification, i.e. at a constant temperature of hybridisation, the melting temperature of the probe with any possible analyte's polymorphism is increased compared to the melting temperature of an unmodified probe with any analyte's polymorphism and the diagnostic assay is for assessing the presence of the analyte in the sample.

The invention concerns the use in a diagnostic hybridisation assay of a molecular beacon probe for lowering the IBL effect due to the possible opening of the stem of the molecular beacons by at least one contaminant present in the amplification enzymes mixture, which assay comprises the steps of contacting a set of primers and a sample containing the nucleic acid analyte to amplify the analyte and detecting the amplified analyte or its complement by means of the probe, wherein the probe's stem comprises:
   one or more nucleotides and/or nucleotide analogues that have an affinity increasing modification, especially 2'-O-methyl nucleotides, and
   one or more unmodified nucleotides.

The invention also concerns the use in a diagnostic hybridisation assay of a probe for lowering:
   the effect of sequence variations in a nucleic acid analyte, and/or
   the IBL effect due to the possible opening of the stem-loop structure of the molecular beacons by way of contaminated enzymes,
which assay comprises the steps of contacting a set of primers and a sample containing the nucleic acid analyte to amplify the analyte and detecting the amplified analyte or its complement by means of the probe, wherein the probe's loop comprises:
   one or more nucleotides and/or nucleotide analogues that have an affinity increasing modification, and
   one or more unmodified nucleotides.
and/or the probe's stem comprises:
   one or more 2'-O-methyl nucleotides that have an affinity increasing modification, especially 2'-O-methyl nucleotides, and
   one or more unmodified nucleotides.

Concerning the lowering of the effect of sequence variations in a nucleic acid assay, the binding between a probe and a target is an equilibrium between unbound target and unbound probe on the one hand and the duplex between the two on the other.

This equilibrium is described by the melting temperature (Tm) of the duplex, which is defined herein as the temperature at which 50% of the probe is bound to the target nucleic acid in a duplex. Shifting the equilibrium towards the duplex can be achieved by an increase in the melting temperature. In an assay this will lead to equal quantification of perfectly matching analytes, a better (i.e. higher) quantification of analytes containing polymorphisms in the sequence that is complementary to the probe and an improved detection of very small amounts of (polymorphic) analytes.

As used herein the term "probe" is intended to comprise a stretch of nucleotides hybridising to the target. Preferably the hybridising part is a stretch of 10-50, more preferably 15-35, most preferably 15-30 nucleotides.

The term "affinity increasing" means that the melting temperature of a duplex between a probe comprising an affinity increasing modification and an analyte is increased as compared to the melting temperature between the analyte and the unmodified probe.

The nucleotides or nucleotide analogues having a modification that increases the affinity of a probe containing them to DNA or RNA targets are preferably selected from the group consisting of 2'-O-derivatized nucleotides, locked nucleic acids (LNAS) and peptide nucleic acids (PNAs). In the case of 2'-O-derivatized nucleotides it is preferably a 2'-O-methyl-nucleotide.

The probe according to the invention is preferably a so-called molecular beacon (MB). These probes recognize their targets with higher specificity than linear probes and can easily discriminate targets that differ from one another by a single nucleotide. By the introduction of one or more nucleotides and/or nucleotide analogues that have an affinity increasing modification, and more particularly in the loop of the molecular beacon, the sensitivity to polymorphisms is lowered because the affinity of the probe to the polymorphic analyte is increased and more accurate results are obtained in the assay. Thus, the modified molecular beacon becomes a very versatile tool for lowering the dependency towards sequence variation of the target in a homogenous assay.

With respect to the IBL effect, the term "Molecular Beacon" probe is intended to comprise a stretch of nucleotides belonging to the sequence of the 3' end of the probe hybridising with the complementary sequence of the probe's 5' end. Preferably the hybridising part is a stretch of 4-15, more preferably 5-10, most preferably 6-8 nucleotides.

The modified nucleotides can be used to synthesize the entire probe or to make a chimeric probe in which only a number of nucleotides is replaced by a modified nucleotide.

The amount of modifications that is minimally necessary to neutralize the mismatches is dependent on the amount of differences between the consensus sequence of an analyte and the sequence of the analyte to be detected. In general, it can be stated that the amount of modifications should be such that the melting temperature of the duplex between the probe and the analyte to be detected should lie above the detection temperature, i.e. the temperature at which the detection is performed.

The amount of modified nucleotides in a probe also depends on the type of modification used. The increase in Tm (the melting temperature of the probe with its target) upon introduction of a single LNA nucleotide in the probe is much higher as compared to the effect of a single 2'-O-methyl-nucleotide. In the Examples it is e.g. demonstrated that the introduction of two LNA nucleotides in the probe increased the Tm with 15° C., while twelve 2'-O-methyl-nucleotides were needed to obtain the same increase in Tm.

Analytes to be detected, such as HIV, may contain so-called "hot spots" that are prone to mutations and thus leading to polymorphisms. When the position of those hot spots or other positions of mismatches of the analyte and the probe are known, such as in the case of known isolates, it is preferred to arrange the nucleotides or nucleotide analogues having an affinity increasing modification around the position of the polymorphism, preferably on conserved positions.

The present invention further relates to a hybridisation assay using a nucleic acid probe to detect a nucleic acid analyte, wherein the probe comprises one or more nucleotides and/or nucleotide analogues that have an affinity increasing modification. The modified nucleotides and/or analogues thereof used in the probe are as defined above.

The hybridisation assays of the invention may be of any kind in which a nucleic acid probe is used to detect a nucleic acid analyte. Such assays may be based on the detection of amplified analytes, such as in PCR-, TMA- or NASBA-based assays. However, the probe can also be used in arrays. The invention can be used both in quantitative and qualitative diagnostic assays in which sequence polymorphisms of the target influence the reliability of the assay.

Diagnostic assays that benefit from the invention are for example assays for detecting viruses, bacteria and other biomarkers as for example HIV, HBV, HCV, HSV, CMV, Ebola, *Legionella, Mycoplasma, Chlamydia, Bordetella*, RSV, MRSA, HSV, TNF-$\alpha$, ER-$\alpha$, as long as these diagnostic assays are characterised in such a way that they make use of the hybridisation between the analyte of interest and the modified oligonucleotide.

The invention also relates to a probe that comprises one or more nucleotides and/or nucleotide analogues that have an affinity increasing modification. The probe is preferably a molecular beacon.

In this application the terms analyte, amplicon and target or target sequence may be used interchangeably. The analyte is the original nucleic acid molecule to be detected. The target sequence is the part of the analyte that is amplified by means of the primers. The amplification leads to formation of amplicons, which are the nucleic acid molecules that are physically detected by hybridisation to the probe. The sequence of the amplicons is the same or complementary to the target sequence within the analyte.

The invention will now be described in the examples and drawings that follow and which are not intended to limit the invention in any way. Then the invention will be further illustrated with reference to the accompanying drawings:

FIG. 1: Schematic representation of a Molecular Beacon allowing detection of *Legionella* bacteria, according to the state of the art, hereafter referred as *Legionella*.

FIG. 2: Schematic representation of an improved Molecular Beacon according to the present invention, that both allows detection of the same *Legionella* bacteria and lowers the IBL effect, hereafter referred as Leg-met1.

FIG. 3: Schematic representation of a Molecular Beacon allowing detection of *Mycoplasma* bacteria, according to the state of the art, hereafter referred as *Mycoplasma*.

FIG. 4: Schematic representation of a first embodiment of improved Molecular Beacon according to the present invention that both allows detection of the same *Mycoplasma* bacteria and lowers the IBL effect, hereafter referred as Myco-met.

FIG. 5: Schematic representation of a Molecular Beacon allowing detection of *Chlamydia* bacteria, according to the state of the art, hereafter referred as *Chlamydia*.

Figure 6:
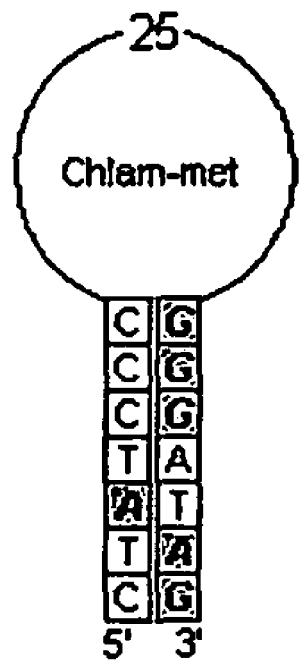

FIG. 6: Schematic representation of an improved Molecular Beacon according to the present invention that both allows detection of the same *Chlamydia* bacteria and lowers the IBL effect, hereafter referred as Chlam-met.

Figure 7:
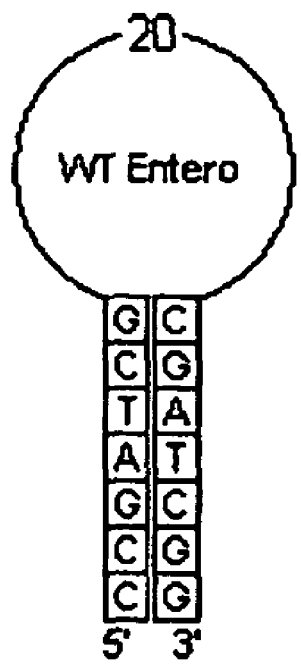

FIG. 7: Schematic representation of a Molecular Beacon allowing detection of wild type of Enterococci bacteria, according to the state of the art, hereafter referred as WT Entero.

Figure 8:
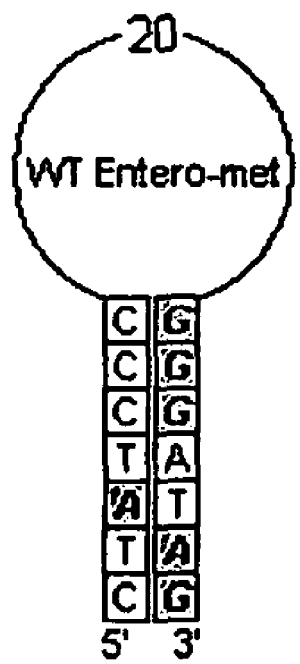

FIG. 8: Schematic representation of an improved Molecular Beacon according to the present invention that both allows detection of the same wild type of Enterococci bacteria and lowers the IBL effect, hereafter referred as WT Entero-met.

Figure 9:
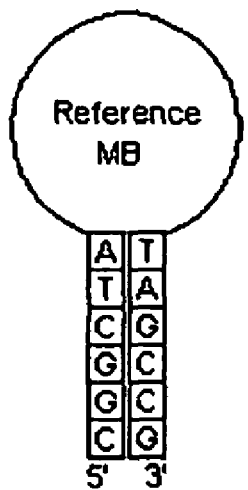
Figure 10:
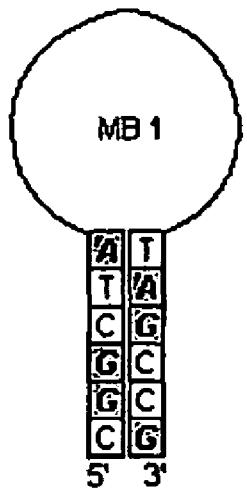
Figure 11:
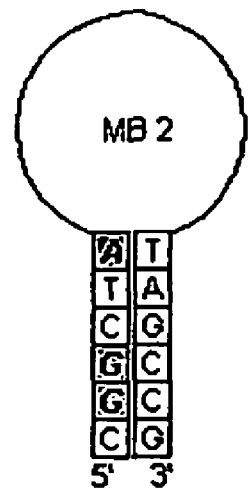
Figure 12:
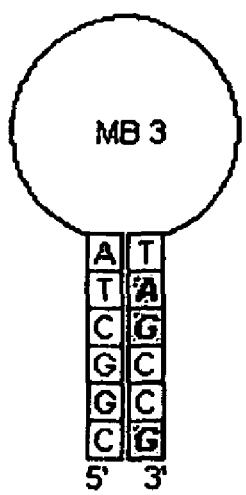
Figure 13:
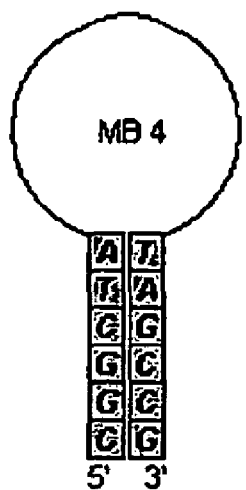
Figure 14:
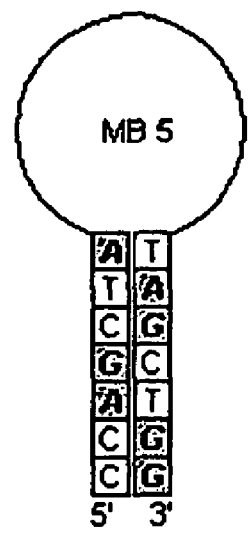
Figure 15:
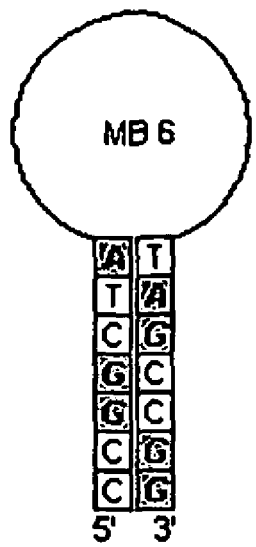
Figure 16:
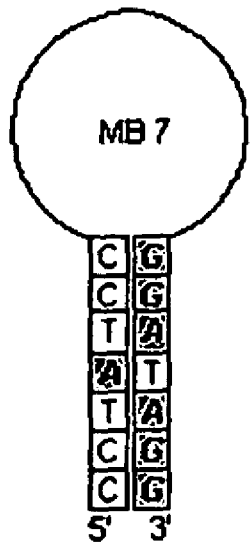
Figure 17:
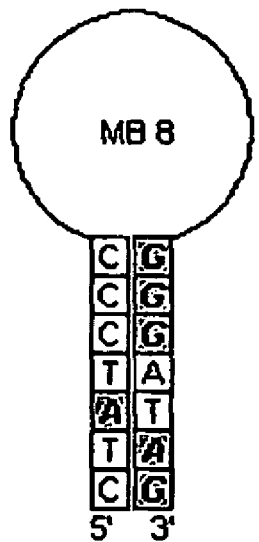
Figure 18:
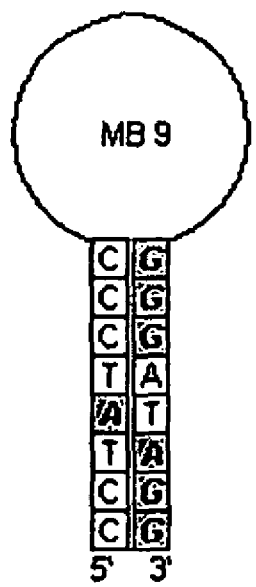
Figure 19:
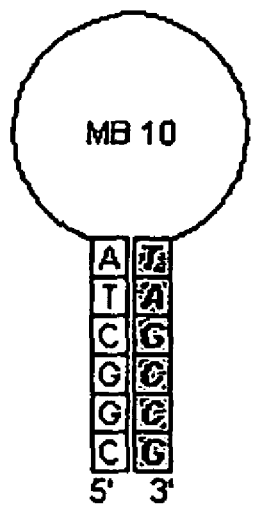

FIG. 9: Schematic representation of a Molecular Beacon allowing detection of HIV, according to the state of the art, incorporating 2'-O-methyl nucleotide neither in the stem nor in the loop, hereafter mentioned as Reference MB.

FIGS. 10-19: Schematic representation of a series of Molecular Beacons allowing detection of HIV, according to the state of the art, hereafter referred as MB 1 to MB 10. Each Molecular Beacon has a different stem that contains 2'-O-methyl derivatives.

Figure 20:
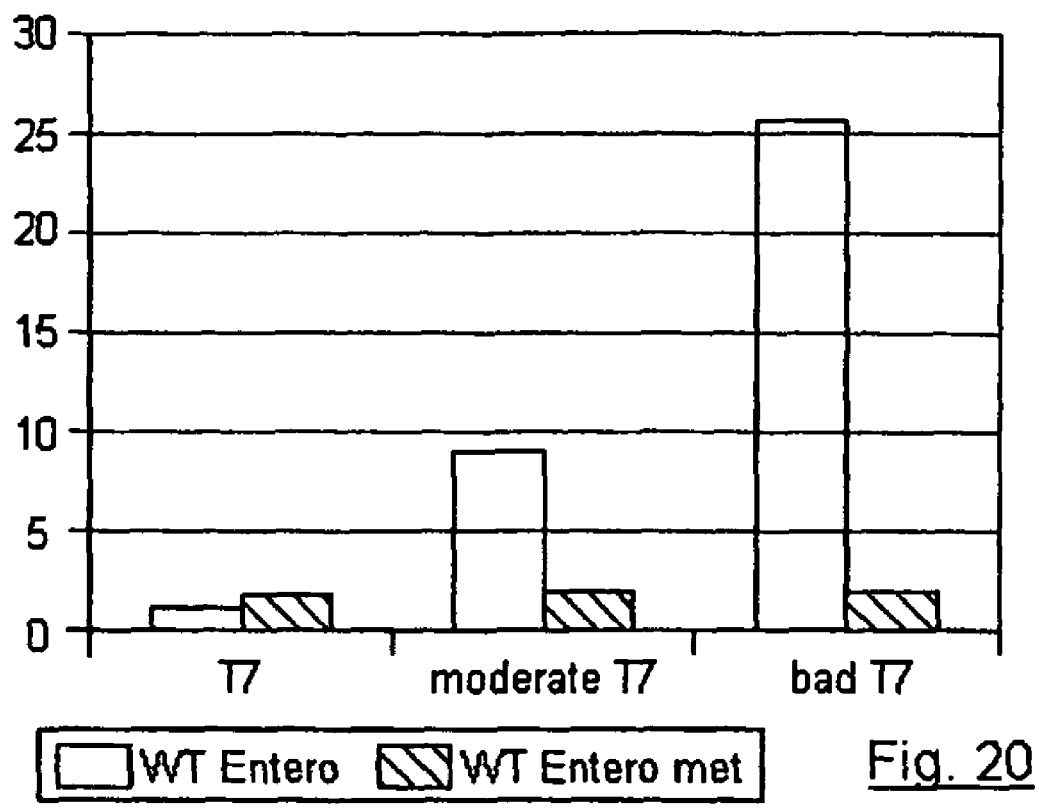

FIG. 20: Bar graph representing the effect of different T7 enzyme batches on the IBL effect.

Figure 21:
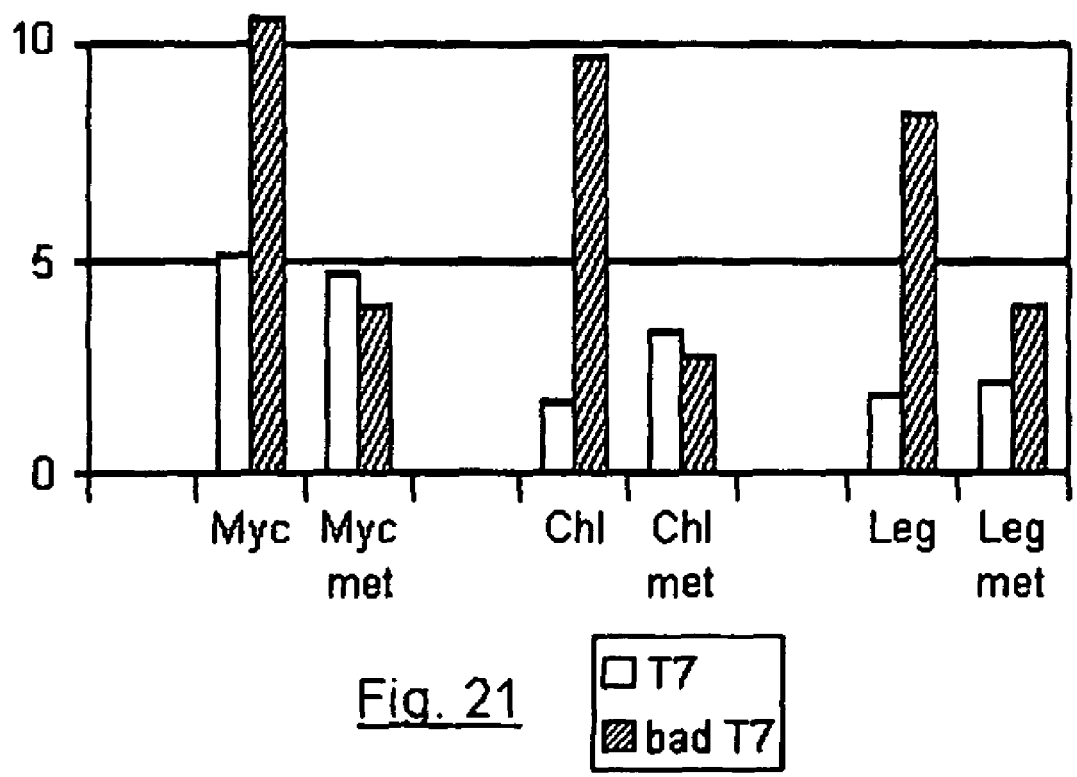

FIG. 21: Bar graph representing the effect of optimal stem structure on the varying IBL effect of different enzyme batches, and representing the comparative study of IBL effect in relation with the structure of various Molecular Beacons used in an assay, i.e. unmodified Molecular Beacons on the one hand and modified Molecular Beacons on the other hand.

In FIGS. 20 and 21, the modified Molecular Beacons incorporate 2'-O-methyl nucleotide in the stem.

In FIGS. 1-8 and 10-19, the modified nucleotides are represented by the corresponding letter, mainly G for guanidine or A for adenine, in bold, italic and underlined.

GENERAL DESCRIPTION OF EXPERIMENTAL DETAILS OF THE EXAMPLES

The examples described below use the conditions and methods mentioned below, unless stated otherwise in the examples.

In the experiments that use amplified RNA material, this material was obtained by amplification of an RNA template (viral lysate), which was extracted and amplified using standard isolation and NASBA amplification conditions.

In every example the reaction conditions were kept identical except for the variation in the type of probe (Molecular Beacon) that was used.

As a model system to determine the improved subtype reactivity, a set of well-characterized viral lysates that represented most of the different subtypes of HIV-1 was used.

If an amplification reaction is being used to generate a quantitative result, the target has been co-amplified using a well-known amount of internal calibrator, which has been added before the isolation. This internal calibrator is detected using another Molecular Beacon with a different colour. From the real-time amplification curves and using specially developed software it is possible to accurately determine the amount of material that is present. Melting temperatures (Tm's) between target and Molecular Beacons were determined by measuring the fluorescence intensity of the mixtures as a function of the increasing temperature. From these melting curves the Tm can be determined. If the excess target is amplicon (RNA) the Tm is referred to as Tm loop RNA. If the target is an excess of synthetic DNA the Tm is referred to as Tm loop DNA. The latter has been determined using synthetic DNA strand, which is complementary towards the Molecular Beacon. In this sequence we have introduced two C's opposite to the Inosines. In the RNA target (amplicon) these positions contain two T's.

Example 1

Effect of the Replacing Nucleotides in a Probe with 2'-O-Methyl Derivatives on the Tm of the Duplex The sequences of the hybridising part of three new and one reference MB are depicted in Table 1. Also the Tm's values of the different Molecular Beacons that have been measured for synthetic DNA and for amplified material (RNA) are shown in Table 1.

TABLE 1

| Name | SEQ ID NO: | Tm loop DNA | Tm loop RNA | Position |   |   |   |   |   |   |   |   |    |    |    |    |    |    |    |    |    |    |    |    |    |    |    |    |
|------|-----|------|------|---|---|---|---|---|---|---|---|---|----|----|----|----|----|----|----|----|----|----|----|----|----|----|----|----|
|      |     |      |      | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
| Ref. | 1 | 58.6 | 48.6 | A | T | C | A | A | T | G | A | G | G | A | I | G | C | T | G | C | A | G | A | I | T | G | G | G | A |
| Me-1 | 2 | 54.7 | 53.8 | A | T | C | *A* | *A* | T | G | *A* | G | G | A | I | G | C | T | G | C | *A* | G | *A* | I | T | G | G | G | A |
| Me-2 | 3 | 58.7 | 62.1 | A | T | C | *A* | *A* | T | *G* | *A* | G | *G* | *A* | I | G | C | T | G | C | A | *G* | *A* | I | T | *G* | *G* | G | A |
| Me-7 | 4 | 59.4 | >65 | A | T | C | *A* | *A* | T | *G* | *A* | G | *G* | *A* | I | *G* | C | T | *G* | C | *A* | *G* | *A* | I | T | *G* | *G* | *G* | A |

*A*, *G* = 2'-O-Me nucleotides of A and G respectively

As can be seen from the data in Table 1, the introduction of 2'-O-methyl derivatives leads to an increased affinity (higher Tm loop RNA) between target RNA and the Molecular Beacon's loop. As expected, this increase is less pronounced for the DNA-Molecular Beacon complex, since 2'-O-methyl derivatives are known to bind stronger with RNA than DNA targets.

Example 2

Effect of Replacing Nucleotides in a Probe with LNAs on the Tm of the Duplex

In Table 2, the hybridizing sequences of two new MB's are shown together with the reference MB. The new MB's contain respectively two and three INA building blocks. Also the Tm values for complementary DNA and for amplified material (RNA) has been measured and results are depicted in the table. From this Table it can be seen that LNA nucleotides increase the Tm of both DNA and RNA complexes. Also it can be seen that the effect on the Tm per modification is much higher as compared to the 2'-O-methyl nucleotides.

The quantification results that were obtained for samples containing an equal amount of target per subtype with three of these Molecular Beacons as compared to our reference Molecular Beacon are shown in Table 4.

TABLE 4

| subtype | Ref MB | LNA2 | Me-2 | Me-7 |
|---|---|---|---|---|
| A | 6.5 | 6.5 | 6.5 | 6.5 |
| G | 4.7 | 5.9 | 6.4 | 6.6 |
| N | 4.3 | 4.6 | 5.2 | 5.3 |
| O1 | 3.3 | 4.9 | 5.4 | 5.9 |
| O3 | 4.9 | 5.8 | 6.3 | 6.2 |

Since the A-subtype fits perfectly with all four Molecular Beacon's, all quantification data are normalized based on this subtype. The other subtypes have been selected since they show sequence variation with the loop-binding region of the Molecular Beacon (see Table 3). As can be seen, the highest quantifications for all five subtypes have been observed with the Me-7 Molecular Beacon derivative.

To investigate the relationship between the better quantification and the Tm loop RNA value (° C.) of the different Molecular Beacon's, the latter were determined for the duplex between the Molecular Beacon derivatives and the NASBA amplicons. This yielded the results shown in Table 5.

TABLE 2

| Name | SEQ ID NO: | Tm loop DNA | Tm loop RNA | Position 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|---|---|---|
| Ref2 | 5 | 45.8 | 57.6 | A | T | C | A | A | T | G | A | G | G | | A | A | G | C | T | G | C | A | G | A | A | T | G | G | G | A |
| LNA1 | 6 | 47.1 | 62.8 | a | T | C | A | A | T | G | A | G | G | | A | A | G | C | t | G | C | A | G | A | A | T | G | G | G | A |
| LNA2 | 7 | 57.5 | >65 | a | T | C | A | A | T | G | A | G | G | | a | A | G | C | t | G | C | A | G | A | A | T | G | G | G | A | a LNA nucleotide

Example 3

Detection of Different HIV-1 Isolates with the Modified Molecular Beacons

The HIV-1 isolates which have been selected to act as a model system to investigate the effect of five sequence polymorphisms in the target RNA sequence are shown in Table 3. These materials were available as viral lysates with a known concentration and have been used in a NASBA amplification with the Molecular Beacon's of example 1 and 2.

TABLE 5

| Tm loop RNA values (° C.) for amplified material (RNA) with several MB's | | | | |
|---|---|---|---|---|
| subtype | ref MB | LNA2 | Me-2 | Me-7 |
| A | 48 | 65 | 62 | 65 |
| G | 45 | 52 | 58 | 65 |

TABLE 3

| Name | SEQ ID NO: | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|---|
| Ref. Molecular Beacon | 1 | A | T | C | A | A | T | G | A | G | G | A | I | G | C | T | G | C | A | G | A | I | T | G | G | G | A |
| Subtype A | 8 | A | T | C | A | A | T | G | A | G | G | A | *A* | G | C | T | G | C | A | G | A | A | T | G | G | G | A |
| Subtype G1 | 9 | A | T | T | A | A | T | G | A | A | G | A | *A* | G | C | T | G | C | A | G | A | G | T | G | G | G | A |
| Subtype N | 10 | A | T | C | A | A | T | G | A | G | G | A | *A* | G | C | A | G | C | A | G | A | C | T | G | G | G | A |
| Subtype O1 | 11 | A | T | C | A | A | T | G | A | T | G | A | *A* | G | C | A | G | C | A | G | A | T | T | G | G | G | A |
| Subtype O3 | 12 | A | T | C | A | A | T | G | A | G | G | A | *A* | G | C | G | G | C | A | G | A | T | T | G | G | G | A |

TABLE 5-continued

Tm loop RNA values (° C.) for amplified material (RNA) with several MB's

| subtype | ref MB | LNA2 | Me-2 | Me-7 |
|---|---|---|---|---|
| N | 42 | 55 | 53 | 60 |
| O1 | 27 | 44 | 44 | 53 |
| O3 | 40 | 52 | 54 | 60 |

As can be seen from Tables 4 and 5 a clear correlation can be observed between a higher Tm loop RNA (between the amplicon and the Molecular Beacon) and a higher quantification.

Example 4

Effect of the Stem Structure on the IBL Reduction

A series of MB's were compared that had an identical hybridising sequence towards an HIV target. The difference between the MB's was the sequence of the stem, and the content and place of 2'-O-methyl derivatives in the stem. The investigated structures are depicted in FIGS. 10-19. FIG. 9 shows the Molecular Beacon that is used as the reference and does not contain 2'-O-methyl derivatives.

All MB's in the experiment described below were supplied to standard NASBA amplification conditions in the absence of target that could be detected with these MB's (no template reactions). The signal of the fluorophore present in the MB was measured as a function of time. From these data the IBL effect is obtained as the increase of the signal over a time period of 60 minutes. The percentage IBL is the increase as compared to the starting signal.

TABLE 6

| MB number | IBL percentage |
|---|---|
| Reference MB | 7% |
| MB 1 | 6% |
| MB 2 | 5% |
| MB 3 | 3% |
| MB 4 | 9% |
| MB 5 | 5% |
| MB 6 | 4% |
| MB 7 | 5% |
| MB 8 | 1.5% |
| MB 9 | 0.5% |
| MB 10 | 10% |

From this table it can be concluded that MB 4 and MB 10, which contain continuous stretches of 2'-O-methoxy nucleotides at either the 3' or the 5' end of the MB do not work optimally. It can also be seen from these data that the design of a stem with a low IBL effect was unexpectedly low for MB 8 and MB 9.

Example 5

Effect of Different T7 Enzyme Batches on the IBL Effect

A MB that was designed for Enterovirus (FIG. 7) was compared with a MB that contained the same hybridizing sequence, but the stem structure was based on the MB 8 (see FIG. 17) from the previous example. The modified MB that was designed for Enterovirus is depicted in FIG. 8.

The two MB's were studied in the experiment described below. They were supplied to standard NASBA amplification conditions in the absence of target that could be detected with these MB's (no template reactions). Reaction conditions were kept identical for both MB's and the variations that were studied was:

1) the effect of the introduction of the new stem in the probe and
2) the effect of three batches of the T7 enzyme in the Nasba reaction.

The three batches were obtained from the same vendor and with the same specific activity. They were different in the observed IBL effect (normal, intermediate, bad in terms of IBL effect (bad being a large amount of unwanted opening of the MB)). The signal of the fluorophore present in the MB was measured as a function of time. From these data the IBL effect is obtained as the increase of the signal over a time period of 120 minutes. The percentage IBL is the increase as compared to the starting signal.

From FIG. 20, it can be seen that for all MB's containing normal deoxynucleotides, the so-called "WT Entero", the unwanted opening of the Molecular Beacons produces a dramatic increase of the IBL effect arizing between the use of intermediate and the use of bad T7's batches. However, the modified MB's containing 2'-O-methoxy's in the stem (FIG. 8), show hardly any influence on the quality of the T7 batches. This clearly shows that it is the quality of the T7 (e.g. at least one contaminant of the T7 could be present) that determines the IBL and not the T7 itself.

Example 6

Effect of Optimal Stem Structure on the Varying IBL Effect of Different Enzyme Batches A second series of MB's that were designed for different targets (*Legionella* (FIG. 1), *Chlamydia* (FIG. 3), *Mycoplasma* (FIG. 5)) were compared with MB's that contained the same hybridising sequence, but the stem structure was based on the MB 8 (see FIG. 17) from the previous example (respectively *Legionella* (FIG. 2) and *Chlamydia* (FIG. 6)). For the Mycoplasma target this was not possible, so a small deviation on the stem structure was made as compared to the MB 8 and modified Molecular Beacons specific for this target were obtained (see FIG. 4).

MB's were studied in pairs (per target) in the experiment described below. They were supplied to standard NASBA amplification conditions in the absence of target that could be detected with these MB's (no template reactions). Reaction conditions were kept identical per set of MB's and the variation that was studied was the introduction of the new stem in the probe and the second variation was the use of two batches of the T7 enzyme in the Nasba reaction. The first batch (referred to as T7) was known to be good, and the second batch (from the same vendor and with the same specific activity) was known to generate more unwanted opening of the Molecular Beacons producing a dramatic increase of the IBL effect. The signal of the fluorophore present in the MB was measured as a function of time. From these data, the IBL effect is obtained as the increase of the signal over a time period of 60 minutes. The percentage IBL is the increase as compared to the starting signal.

From FIG. 21, it can be seen that for all MB's containing normal deoxynucleotides, the bad T7 results in a higher effect of the unwanted IBL. However, the modified MB's containing 2'-O-methoxy's in the stem showed hardly any influence on the quality of the T7. In other words, the use of methoxy derivatives in the stem structure makes the MB less vulnerable to the enzyme quality.

The invention claimed is:

1. A molecular beacon probe, comprising: a stem comprising one or more unmodified nucleotides, and in the 3' strand of the stem, one or more nucleotides or nucleotide analogues having an affinity increasing modification, wherein said one or more nucleotides or nucleotide analogues are selected from the group consisting of a 2'-O-derivatized nucleotide, a locked nucleic acid, and a peptide nucleic acid, wherein each base pair of said stem comprises no more than one 2'-O-derivatized nucleotide, and further wherein said molecular beacon probe has better stability and does not open spontaneously in the presence of contaminants present in an amplification enzyme mixture as compared to a molecular beacon probe without said stem.

2. The molecular beacon probe as claimed in claim 1, wherein the 2'-O-derivatized nucleotide is a 2'-O-methyl-nucleotide.

3. The molecular beacon probe as claimed in claim 1, wherein at least one base pair of said stem contains no nucleotide or nucleotide analogue having an affinity increasing modification.

4. The molecular beacon probe as claimed in claim 1, wherein only one base pair of said stem comprises no nucleotide or nucleotide analogue having an affinity increasing modification.

5. A kit for performing a diagnostic amplification assay, comprising the appropriate primers, polymerase(s) and reagents for performing amplification of an analyte to be diagnosed and the molecular beacon probe of claim 1 for detecting the amplified analyte.

6. A molecular beacon probe comprising a stem and a loop, wherein said loop comprises: one or more nucleotides and/or nucleotide analogues that have an affinity increasing modification, and one or more unmodified nucleotides; and said stem comprises one or more unmodified nucleotides, and in the 3' strand of the stem, one or more 2'-O-methyl nucleotides, wherein each base pair of said stem comprises no more than one 2'-O-methyl nucleotide, wherein the sensitivity of said molecular beacon probe with said loop to polymorphisms in the target nucleic acid sequence is lowered as compared to a molecular beacon probe without said loop and wherein the spontaneous opening of the molecular beacon probe with said stem in the presence of contaminants present in an amplification enzyme mixture is lowered as compared to a molecular beacon probe without said stem.

7. The molecular beacon probe as claimed in claim 6, wherein the nucleotides or nucleotide analogues having an affinity increasing modification are selected from the group consisting of 2'-O-derivatized nucleotides, locked nucleic acids, and peptide nucleic acids.

8. The molecular beacon probe as claimed in claim 6, wherein at least one base pair of said stem contains no nucleotide or nucleotide analogue having an affinity increasing modification.

9. The molecular beacon probe as claimed in claim 6, wherein only one base pair of said stem comprises no nucleotide or nucleotide analogue having an affinity increasing modification.

10. A kit for performing a diagnostic amplification assay, comprising the appropriate primers, polymerase(s) and reagents for performing amplification of an analyte to be diagnosed and the molecular beacon probe of claim 6 for detecting the amplified analyte.

11. A molecular beacon probe, comprising: a stem comprising one or more nucleotides or nucleotide analogues having an affinity increasing modification, wherein said one or more nucleotides or nucleotide analogues are selected from the group consisting of a 2'-O-derivatized nucleotide, a locked nucleic acid, and a peptide nucleic acid, and one or more unmodified nucleotides, wherein each base pair of said stem comprises no more than one 2'-O-derivatized nucleotide and only one base pair of said stem comprises no nucleotide or nucleotide analogue having an affinity increasing modification, and further wherein said molecular beacon probe with said stem has better stability and does not open spontaneously in the presence of contaminants present in an amplification enzyme mixture as compared to a molecular beacon probe without said stem.

12. The molecular beacon probe as claimed in claim 11, wherein the 2'-O-derivatized nucleotide is a 2'-O-methylnucleotide.

13. A molecular beacon probe comprising a stem and a loop, wherein said loop comprises: one or more nucleotides and/or nucleotide analogues that have an affinity increasing modification, and one or more unmodified nucleotides; and said stem comprises: one or more 2'-O-methyl nucleotides, and one or more unmodified nucleotides, wherein each base pair of said stem comprises no more than one 2'-O-methyl nucleotide and only one base pair of said stem comprises no nucleotide or nucleotide analogue having an affinity increasing modification,
wherein the sensitivity of said molecular beacon probe with said loop to polymorphisms in a target nucleic acid sequence is lowered as compared to a molecular beacon probe without said loop and wherein the spontaneous opening of said molecular beacon probe with said stem in the presence of contaminants present in an amplification enzyme mixture is lowered as compared to a molecular beacon probe without said stem.

14. A molecular beacon probe, comprising: a stem comprising one or more unmodified nucleotides, and in each strand of said stem, at least one nucleotide or nucleotide analogue having an affinity increasing modification, wherein said at least one nucleotide or nucleotide analogue is selected from the group consisting of a 2'-O-derivatized nucleotide, a locked nucleic acid, and a peptide nucleic acid, wherein each base pair of said stem comprises no more than one 2'-O-derivatized nucleotide, and further wherein said molecular beacon probe with said stem has better stability and does not open spontaneously in the presence of contaminants present in an amplification enzyme mixture as compared to a molecular beacon probe without said stem.

15. The molecular beacon probe as claimed in claim 14, wherein the 2'-O-derivatized nucleotide is a 2'-O-methylnucleotide.

16. The molecular beacon probe as claimed in claim 14, wherein only one base pair of said stem comprises no nucleotide or nucleotide analogue having an affinity increasing modification.

17. A molecular beacon probe comprising a stem and a loop, wherein said loop comprises: one or more nucleotides and/or nucleotide analogues that have an affinity increasing modification, and one or more unmodified nucleotides; and said stem comprises: one or more unmodified nucleotides, and in each strand of said stem, at least one 2'-O-methyl nucleotide, wherein each base pair of said stem comprises no more than one 2'-O-methyl nucleotide, wherein the sensitivity of said molecular beacon probe with said loop to polymorphisms in a target nucleic acid sequence is lowered as compared to a molecular beacon probe without said loop and wherein the spontaneous opening of said molecular beacon probe with said stem in the presence of contaminants present in an amplification enzyme mixture is lowered as compared to a molecular beacon probe without said stem.

18. The molecular beacon probe as claimed in claim 17, wherein only one base pair of said stem comprises no nucleotide or nucleotide analogue having an affinity increasing modification.

19. A method for assessing the presence of a nucleic acid analyte in a sample using a molecular beacon probe, the method comprising contacting a set of primers and a sample containing the nucleic acid analyte to amplify the analyte; and detecting the amplified analyte or its complement using the molecular beacon probe of claim 1, thereby assessing the presence of nucleic acid analyte in the sample.

20. The method of claim 19 wherein the method is a homogenous assay.

21. The method of claim 19 wherein the method is a heterogeneous assay.

22. A method for assessing the presence of a nucleic acid analyte in a sample using a molecular beacon probe, the method comprising contacting a set of primers and a sample containing the nucleic acid analyte to amplify the analyte; and detecting the amplified analyte or its complement using the molecular beacon probe of claim 6, thereby assessing the presence of nucleic acid analyte in the sample.

23. The method of claim 22 wherein the method is a homogenous assay.

24. The method of claim 22 wherein the method is a heterogeneous assay.

* * * * *